United States Patent

Schmitt, Jr. et al.

[11] 4,081,370
[45] Mar. 28, 1978

[54] USE OF CARBON PARTICULATES WITH CONTROLLED DENSITY AS ADSORBENTS

[75] Inventors: Joseph Lawrence Schmitt, Jr., Bethel, Conn.; Philip Leroy Waker, Jr., State College, Pa.; George Augustus Castellion, Stamford, Conn.

[73] Assignee: American Cyanamid Company, Stamford, Conn.

[21] Appl. No.: 770,875

[22] Filed: Feb. 22, 1977

Related U.S. Application Data

[60] Division of Ser. No. 688,508, May 20, 1976, Pat. No. 4,029,600, and a continuation-in-part of Ser. No. 559,933, Mar. 19, 1975, abandoned.

[51] Int. Cl.² ............................................. B01D 15/00
[52] U.S. Cl. ..................................................... 210/39
[58] Field of Search ....................... 252/421, 444, 445; 210/36, 39, 40, 502, 506, 510

[56] References Cited

U.S. PATENT DOCUMENTS

| | | | |
|---|---|---|---|
| 3,533,961 | 10/1970 | Voet et al. | 252/421 |
| 3,763,040 | 10/1973 | Timpe et al. | 210/40 |
| 3,779,909 | 12/1973 | Wisfeld et al. | 210/40 |
| 3,953,345 | 4/1976 | Saito et al. | 210/40 |

Primary Examiner—Charles N. Hart
Assistant Examiner—Ivars Cintins
Attorney, Agent, or Firm—William J. van Loo

[57] ABSTRACT

Carbon particulates comprising carbon black spheres and a carbon binder having large pores as well as desirable pore size distributions are disclosed which are useful as selective adsorbants. A method of preparation and various uses are also disclosed.

3 Claims, 1 Drawing Figure

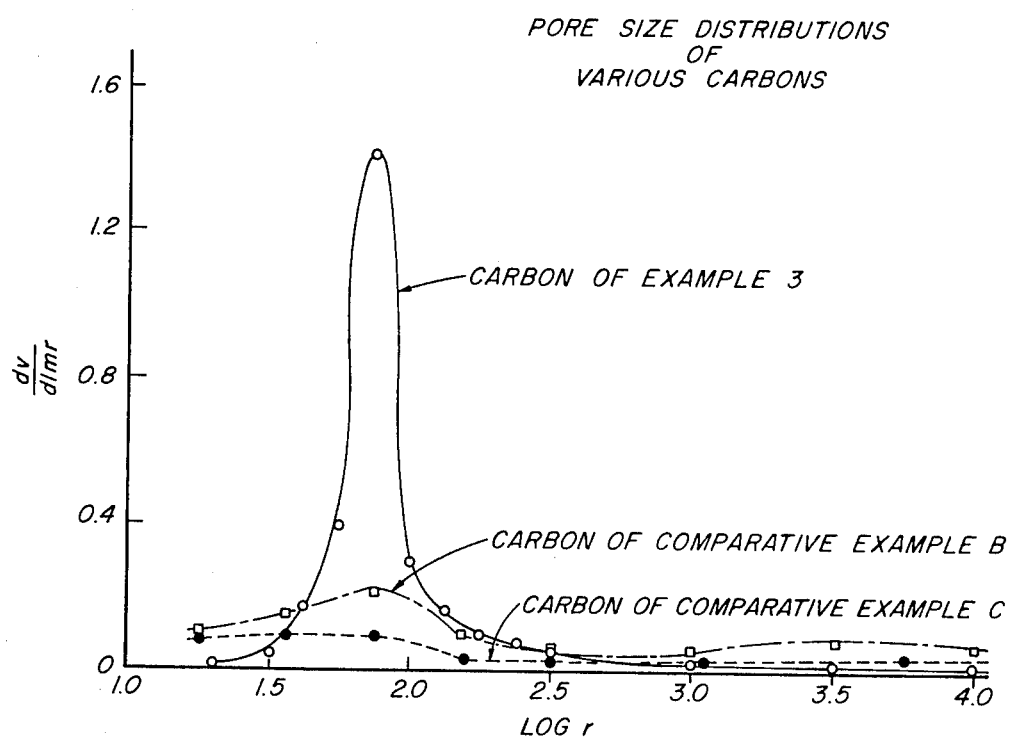

USE OF CARBON PARTICULATES WITH CONTROLLED DENSITY AS ADSORBENTS

This is a division of application Ser. No. 688,508 filed May 20, 1976 now U.S. Pat. No. 4,029,600, which is a continuation-in-part of application Serial No. 559,933, filed March 19, 1975, now abandoned.

This invention relates to porous carbon particulates and, more particularly, is concerned with such particulates comprising carbon black spheres in packed relationship and a carbon binder, said particulates being useful as selective adsorbents and catalyst supports.

This application is directed to the porous carbon particulates, to the method of preparation thereof, and to use thereof as selective adsorbents. Copending application Ser. No. 559,997, now U.S. Pat. No. 3,978,000 filed on March 19, 1975, is directed to catalyst compositions comprising the porous carbon particulates as supports carrying active catalytic materials thereon and use of such catalyst compositions in certain catalytic reactions.

Carbons containing macropores can be used as adsorbents where large molecules are to be adsorbed, as in the decolorization of sugar or the treatment of waste waters.

Porous carbons have been obtained in the prior art by activation of a suitable material, such as coal or wood charcoal, with oxidizing agents. These oxidizing agents, e.g. $O_2$, $CO_2$, steam, and the like, react away portions of the carbon, leaving behind pores. Carbons with controlled pore size distribution cannot be made by this procedure since new pores are continuously formed while existing pores are constantly enlarged. This results in a wide range of pore sizes, including many small pores, i.e. well below 20 angstrom units, as activation is continued. Thus, it has been difficult to obtain porous carbons containing predominantly transitional pores (diameter 20–200 angstrom units) as well as carbons having a narrow range of specific pore sizes.

In addition to the problem of controlling pore size distribution in prior art carbons, the reacting away of carbon to provide pores creates additional problems. When large pores are desired in the carbon, the reacting away of the carbon weakens the mechanical strength of the final structure. The reacting away of carbon increases the percent of ash present on the residual carbon and ash contents of 5–10 weight percent are normal. In addition, carbons prepared by the prior art procedure contain many surface groups containing oxygen. Such groups have a profound effect on its surface chemistry. Pure carbon is hydrophobic but the presence of bound oxygen reduces the hydrophobicity and causes the surface to possess a polar nature. As a consequence, the surface is less effective as an adsorbent for hydrophobic substances and more effective as an adsorbent for polar compounds. If, for example, it were desired to adsorb a non-polar substance such as benzene from a solution also containing a polar substance such as ethanol, carbons having surface groups containing oxygen would be considerably less effective adsorbents for benzene than carbons not containing such surface groups.

The preparation of carbon structures by other procedures is also known in the prior art. In many instances, however, such structures contain significant amounts of material other than carbon. In other instances the particular carbon structure is prepared for uses other than as selective adsorbents so that no specific requirements as to porosity or pore size distribution are necessary.

In U.S. Pat. No. 3,533,961, Voet et al. issued Oct. 13, 1970, for example, large carbon particles of low surface area are mixed with powdered coal tar pitch, and the mixture in the presence of water is agglomerated to form spheres. The spheres are then dried, carbonized, and activated with steam to provide a granulated activated carbon. Such carbons have low crush strength relative to their porosity because the structure has not been compacted by pressure such as in molding. Furthermore, the carbons have low values of pore volume and surface area until activated. However, activation of such carbons does not provide an appreciable portion of its surface area in the form of pores of large radius, i.e. above about 20 angstrom units in radius because of the fact that such activation continuously forms new pores, as previously mentioned.

Thus, there continues to exist the need for substantially pure carbon structures that have desirable levels of porosity or controlled pore size distribution and are free of or improved with respect to deficiencies of the prior art carbons. Such a development would fill a long-felt need in the art and provide a notable advance in the art.

Accordingly, it is a primary object of the present invention to use a porous carbon structure having pores of controlled size distribution as an adsorbent. Other objects will become apparent from the description which follows.

In accordance with the present invention, there is provided a porous carbon particulate comprising carbon black spheres bonded in compacted relationship by a carbonized binder, said spheres having an average diameter in the range of about 80 to 5000 angstrom units and a surface area of at least 100 square meters per gram, and said particulate having a pore volume of at least 0.2 cubic centimeters per gram, a surface area of at least 100 square meters per gram, said particulate surface area being equal to or less than the surface area of said spheres, and a pore size distribution such that at least 45% of its total surface area is in pores of radius equal to or greater than 20 angstrom units.

Preferably, the particulate will have a composition of at least 99 weight percent carbon. In preferred embodiments, the carbon particulate will exhibit pore volume of about 0.4–1.1 cubic centimeters per gram, surface area of at least about 200 square meters per gram, and at least about 40% of said surface area will be in the form of pores of 40–200 angstrom units.

In accordance with the present invention, there is also provided a process for preparing the above-described carbon particulate which comprises uniformly admixing carbon black spheres having diameters in the range of about 80 to 5000 angstrom units and a surface area of at least 100 square meters per gram with a carbonizable binder compacting the resulting mixture into a suitable structure and carbonizing said binder.

In accordance with the present invention, pores of the carbon particulate are formed by compacting together of suitable carbon black spheres and binding the spheres together in compacted relationship with carbon binder. The use of the carbon binder allows the carbon particulate to possess improved mechanical strength. When the carbon black spheres compacted and bonded together are of substantially the same size and relatively small, a narrow range of pore size distribution will arise and the particulate will possess good mechanical strength. The particular range of pore sizes and distribution thereof will vary with particle size of the carbon black spheres selected and the variations which occur within a designated size. Thus, if larger carbon black spheres are used, the interstital space or pores will be larger, while the use of spheres of varying diameter will result in a wide range of pore sizes.

In accordance with the present invention, there is also provided a process of adsorbing adsorbable materials from solution which comprises contacting said solution with the carbon particulate of the present invention. In one embodiment of such process, the particulate is formed as a bed through which the solution is passed. In an alternative embodiment, the particulate is contacted with the solution for an effective time period after which the particulate is removed by filtration.

The present invention, by use of the carbon binder, provides carbon particulates of good mechanical strength in conjunction with large pore sizes. In prior art carbon structures, when large pores are desired, extensive oxidation is necessary to provide the pores and the loss of carbon thus occasioned greatly weakens the resulting structure.

The carbon particulates of the present invention will, in preferred embodiments, have a large surface area resulting from pores in the transitional range, i.e. 20 to 200 angstrom units, and from macropores, i.e. pores greater than about 200, for example about 250, angstrom units. The number of pores in the transitional and macropore range will be much greater than can be achieved by the prior art procedures.

Since the carbon black spheres used in the fabrication of carbon particulates of the present invention are of a high state of purity, the resulting particulates will be much purer than prior art carbon structure obtained by the conventional oxidation procedures. Normally, the prior art structures contain from 5–10 weight percent of ash. In addition, since the carbon particulates of the present invention are prepared without the use of oxidizing agents to react away carbon, the carbon particulates of the present invention will contain considerably less surface oxygen-containing groups than the conventional carbon structures.

Carbon particulates of the present invention because of their desirable porosity and pore size distribution are very useful as selective adsorbents, particularly when large molecules are involved. The low content of surface groups containing oxygen increases the effectiveness of the carbon particulates in applications involving non-polar compounds that are to be selectively adsorbed.

Carbon blacks are formed by the thermal decomposition of gaseous and liquid hydrocarbons. Two main manufacturing processes are employed. In the channel process, carbon black is collected by impingement of small, natural gas diffusion flames on cool channel iron surfaces. By altering the size of the burner tip and its distance from the channel surface, the particle size of the carbon black can be varied.

The furnace combustion process, which currently produces the greater amount of carbon black, uses larger diffusion flames to combust natural gas and/or liquid hydrocarbons in firebrick-lined furnaces. Carbon black with considerably larger particle size than channel black can be produced.

Carbon particles useful in the present invention may be of any shape that can be packed and bonded together to provide particulates which have the desired porosity.

Particularly suitable are available carbon blacks made by the above processes, which generally have an average diameter from about 80 to 5000 angstrom units and a surface area of at least 100 square meters per gram but which can be much larger depending upon the specific preparative method employed. These carbon blacks are revealed by electron photomicrographs to consist of ultimate particles which appear to be essentially spherical. For convenience, therefore, in the present application and claims, the carbon black particles are referred to as spheres but it is to be understood that the present invention is inclusive of other shapes, such as oval-shapes, round-cornered squares, rectangles, triangles, and the like as long as such particles upon packing and bonding give rise to the porosity desired.

Carbon black spheres useful in the present invention may be selected from any that are commercially available. Selection is based on the porosity and pore size distribution desired in the carbon particulate to be provided in accordance with the present invention. When small pores of a narrow pore size distribution are desired, carbon black spheres of small particle size and narrow variation in particle size are selected. When large pores are desired, carbon black spheres of large particle size are selected. When a wide range of pore sizes are desired, mixtures of carbon black spheres of varying particle sizes are selected. It is to be noted that large carbon black spheres can provide a wide range of pore size distribution as well as large pores.

In addition to the carbon black spheres, it is also necessary to employ a binder for the spheres that are to become arranged in packed relationship. The binder is a substance which when heat-treated in an inert or non-oxidizing atmosphere yields a high proportion of carbon. Generally, a carbon yield greater than about 20 weight yield is desirable when heat-treatment is carried out at 600° C. in an atmosphere of nitrogen. Carbon yield is the weight of carbon residue divided by the weight of starting material and multiplied by 100. Materials which meet this qualification include polymers such as poly(furfuryl alcohol), polyacrylonitrile; resins such as phenol-formaldehyde, phenol-benzaldehyde; and certain natural materials such as coal tar pitch. Preferably the binder will be a thermosetting resin. Enough binder is required to hold the carbon structure together after carbonization of the binder. Normal ratios of carbon black spheres to binder will be from about 10:1 to 01:1, preferably 5:1 to 1:1, on a weight basis based on the amounts of materials employed prior to heat-treatment to carbonize the binder.

It is preferable to employ a mixing medium to provide intimate mixing of the binder and the carbon black spheres. Preferably the mixing medium will be a solvent for the binder but it is possible to employ the binder in emulsified or dispersed form in the mixing medium. The mixing medium should be volatile enough so that gentle heating (100°–150° C.) will effect volatilization and eliminate the possibilities that the mixing medium will interfere with or take part in carbonization of the binder. Suitable mixing media include acetone, methyl isobutyl ketone and other ketones, benzene, pyridine, water and the like. The amount of mixing medium should be enough to ensure intimate mixing and may vary widely. Generally the amount of mixing medium will be such as to provide the binder as about a 5 to 50 weight percent solution or emulsion, preferably about 10 to 20 weight percent solution.

Once the carbon black spheres, the binder and optional mixing medium are selected and intimately admixed the resulting composition is processed so as to compact the carbon black particles into a suitable structure. Such compacting may involve extrusion, pelletizing, pilling, tabletizing and such other forms of molding as are conventionally employed in forming structured particles. It is also possible to employ rolling mills and flakers to provide a formed structure of packed carbon particles although such procedures do not usually form uniform particles as in the case of molding. It is generally preferred to employ extrusion to obtain the carbon structure. The carbon structure thus obtained is referred to as a "green body". The green body is subjected to carbonization at elevated temperature in an inert or non-oxidizing atmosphere so as to convert the binder to carbon. The resulting carbon structure may be utilized in the form obtained or it may be subdivided by crushing or grinding, if desired. It can also be further modified by treatment with an oxidizing agent, if desired, although it is generally preferable to take advantage of the desirable properties achieved in the absence of oxidation of the carbon structure.

As has been indicated, the carbon structure of the present invention can be prepared in a wide variety of pore volume and pore size distribution. In particular embodiments, the carbon structures will have a larger surface area in the large pore region than previously available carbons, the large-pores occurring in a narrow size range, if desired. Such a carbon structure is very useful as a selective adsorbent when large molecules are to be adsorbed. This type of carbon, by virtue of its method of preparation, will also have a much lower ash content (impurity level) than conventional oxidized carbons.

The invention may be further understood by references to the FIGURE which shows comparative pore size distribution of various carbons.

The invention is more fully illustrated by the examples which follow wherein all parts and percentages are by weight unless otherwise specified.

In the examples which follow reference is made to certain physical properties of the particulates obtained. These properties are obtained in accordance with conventional methods employed in the art of catalyst supports.

Pore volume may be obtained by mercury penetration or water adsorption. The latter is a preferred method because it is easily performed and has an accuracy of ± 10%. In the water absorption procedure, a small quantity of support (1-2 gram) is weighed into a glass dish. Water is slowly poured onto the support until no more is absorbed. Excess droplets are carefully removed by blotting and a reweighing is made. Assuming that one gram of water occupies 1 cubic centimeter, the pore volume is calculated from the initial and final weights of the support.

Surface area is measured by a low temperature nitrogen adsorption technique which is reported in J. Am. Chem. Soc., 60, 309 (1938), with modifications as reported in Anal. Chem. 30, 1387 (1958) and Anal. Chem. 34, 1150, (1962). The percentage of surface area in pores of specified size is obtained from low temperature desorption data using a cylindrical pore model.

Comparative Example A

Into 12 milliliters of water were added 10 grams of carbon black spheres having an average particle diameter of 120 angstom units and a surface area of 850 square meters per gram. After hand mixing, the resulting composition was extruded through a hole of 1/16 inch diameter using a piston-type extruder operating at a pressure of 2000 pounds per square inch gauge. The resulting extrudates were dried in air at 110° C. and then heated in flowing nitrogen at 600° C. for 1 hour. The product was obtained in the form of cylindrical pellets. Properties are given in Table I.

EXAMPLE 1

A furfuryl alcohol polymer was prepared by mixing 200 milliliters of furfuryl alcohol, 200 milliliters of water, and 1 milliliter of concentrated $H_2SO_4$. The mixture was heated at 90° C. for 10 minutes. The dark polymer obtained was washed twice with water and then stored in a closed bottle.

In 100 ml. of acetone was dissolved 10 grams of the furfuryl alcohol polymer thus prepared. The resulting solution was added to 40 grams of carbon black spheres having an average particle diameter of 120 angstrom units and a surface area of 850 square meters per gram. The resulting composition was thoroughly mixed using a Sunbeam Mixmaster. The mixture was then extruded through a hole of 1/16 inch diameter using a piston-type extruder operating at 800-2000 pounds per square inch gauge.

The resulting extrudates were heated overnight at 110° C. to volatilize all of the acetone present and then carbonized in a tube furnace under flowing $N_2$. A temperature of 600° C. was reached in about 1 hour and held for 1 hour. The extrudates were then cooled to room temperature under flowing nitrogen. The product was obtained in the form of cylindrical pellets. Properties are also give in Table I.

EXAMPLE 2

The procedure of Example 1 was repeated in every essential detail except that 20 grams of a commercial phenol-formaldehyde resin was substituted for the furfuryl alcohol polymer of Example 1 and the extrusion pressure was 2400 psig. Properties of the resulting pellets are also given in Table I.

TABLE I

| | Properties Of Carbon Particulates | | | |
|---|---|---|---|---|
| EXAMPLE | BINDER | BINDER AMOUNT[1] | PORE VOLUME[2] | CRUSH STRENGTH[3] | SURFACE AREA[4] |
| Comparative A | None | 0 | 1.00 | 1.2 | 755 |
| 1 | Poly(furfuryl Alcohol) | 25 | 0.99 | 5.4 | 530 |
| 2 | Phenol-Formaldehyde | 50 | 0.62 | 7.7 | 358 |

TABLE I-continued

| | | Properties Of Carbon Particulates | | | |
|---|---|---|---|---|---|
| EXAMPLE | BINDER | BINDER AMOUNT[1] | PORE VOLUME[2] | CRUSH STRENGTH[3] | SURFACE AREA[4] |
| | Resin | | | | |

Notes:
[1] Weight % based on weight of carbon black
[2] Cubic centimeters per gram
[3] Pounds
[4] Square meters per gram Table I illustrates the importance of the binder in obtaining improved particulate strength. It can be seen that use of 25% binder resulted in a 4.5 fold increase in strength with essentially no loss in pore volume. Use of higher amounts of binder result in further increases in strength but results in lower pore volumes. Thus, if lower pore volumes can be tolerated, higher binder usage may be desirable. The particulates of Examples 1 and 2 had at least 45% of their surface area in pores greater than 20 angstrom units.

EXAMPLE 3

In 75 ml. of acetone were dissolved 7.5 grams of poly (furfuryl alcohol) prepared as in Example 1. To this solution were added 30 grams of the carbon black spheres as used in Example 1. After thorough mixing, the resulting composition was extruded as in Example 1 using 250-500 psig extrusion pressure. The extrudates were dried overnight and then carbonized as in Example 1. Properties of the resulting pellets are given in Table II and the FIGURE.

Comparative Example B

For comparison purposes, a commercially available carbon prepared by oxidation of carbon was selected. This carbon is sold under the tradename Darco Granular and was in the form of grains 12 × 20 mesh. Properties are also given in Table II and the FIGURE.

Comparative Example C

For comparative purposes, another commercially available carbon prepared by oxidation of carbon was selected. This carbon is sold under the tradename Columbia Type L and was in the form of grains of 12 × 20 mesh. Properties are also shown in Table II and the FIGURE.

TABLE II

| | Properties of Carbon Particulates | | |
|---|---|---|---|
| Example | Pore Volume[1] | Surface Area[2] | Crush Strength[3] |
| 3 | 0.92 | 530 | 3.1 |
| Comparative B | 1.07 | 580 | 2.3 |
| Comparative C | 0.86 | 1235 | 5.7 |

Notes:
[1] cc/gram
[2] M²/gram
[3] lbs.

In the FIGURE are shown the pore size distribution for the carbons of Example 3, Comparative Example B, and Comparative Example C as obtained by mercury porosity [see Orr, C., Powder Technol. 3, 117 (1969-70)]. In the FIGURE, the change in pore volume with respect to the change in the natural logarithm of the pore radius is plotted against the logarithm to the base 10 of the pore radius. As can be seen by the FIGURE, the pore size ditribution curves illustrate the major difference of carbon particulates of the present invention, which have many more pores in the region of radii of 40-100 angstrom units while many of the pores of the comparative carbons are too small to be measured by mercury penetration.

EXAMPLES 4-7

In these examples, a series of carbon particulates were prepared following the procedure of Example 3 in every essential detail except that carbon black spheres of different particle sizes were employed in separate preparations. Properties of the carbon black spheres employed and of the resulting carbon particulates are given in Table III.

TABLE III

| | CARBON BLACK SPHERES | | | EXTRUDATE PROPERTIES | | | |
|---|---|---|---|---|---|---|---|
| EXAMPLE | AVERAGE DIAMETER[1] | SURFACE AREA[2] | SPHERES/ BINDER RATIO[3] | SURFACE AREA[2] | PORE VOLUME[4] | RADII PEAKS AT[1] | % SURFACE AREA IN PORES OF 20 A RADIUS OR GREATER |
| 4 | 120 | 850 | 4 | 550 | 0.95 | 12, 65 | 55 |
| 5 | 300 | 230 | 3 | 108 | 0.43 | 18 + Broad Dist. To > 200 | 54 |
| 6 | 160 | 380 | 3 | 229 | 0.80 | 95 | 76 |
| 7 | 150 | 550 | 4 | 364 | 0.95 | 18, 95 | 60 |

Notes:
[1] Angstrom units
[2] Meters²/gram
[3] Based on weight before carbonization
[4] cc/gram It can be seen from Table III that the physical properties of the carbon particulates of the present invention may be varied by varying the size of the carbon black spheres or the ratio of spheres to binder. It is evident that the pore size of the carbon particulates can be shifted toward larger sizes by using carbon black spheres of larger average particle size.

EXAMPLES 8–10

To 40 grams of carbon black spheres used in Example 1 and 20 grams of phenol-formaldehyde resin (Durez 7031 A - Hooker) after mixing were added 50 ml of $H_2O$. The mixture was thoroughly mixed and divided into three portions. A first portion, Example 8 was extruded using a screw-type extruder and an extrusion die containing ⅛ in. holes. Properties of the extrudates obtained are given in Table IV.

A second portion, Example 9 were pelletized using a Parr pellet press having a ⅛ in. cylindrical die and punch which operated at hand pressure. Properties of the pellets obtained are also given in Table IV.

A third portion Example 10, was fed through a Farrel 2-roll mill set at 1/16 in. between rolls to form flakes. Properties of the flakes are also given in Table IV.

In each of these examples, after the particulates were shaped by the compacting procedure indicated, they were allowed to dry at room temperature over a period of several days and then carbonized at 600° C. for 1 hour in $N_2$ prior to property determinations.

Comparative Example D

The procedure of Example 1 of U.S. Pat. No. 3,533,961 was followed with exceptions as noted. The carbon black employed was Statex G, GPF, which had a particle size of 60 millimicrons. The coal tar pitch had a softening point of 120°–130° C. Agglomerates were formed using a simulated pin-mixer and spheres formed were screened to provide the 3/16 in. × 10 mesh fraction. The agglomerates were carbonized at 600° C. for 1 hour in $N_2$ but were not activated with steam. Physical properties are given in Table IV.

Comparative Example E

The procedure of Example 4 of U.S. Pat. No. 3,533,961 was followed with exceptions as noted. The carbon black employed was Philblack O, HAF, which had a particle size of 26 millimicrons. The coal tar pitch had a softening point of 120°–130° C. Agglomerates were prepared and screened and then carbonized as in Comparative Example D. No activation with steam was effected. Physical properties are given in Table IV.

the present invention was that prepared in accordance with Example 4. Representative of prior art adsorbents were those of Comparative Examples B and C.

A. Methylene Blue

Adsorption of the dye methylene blue from aqueous solution is dependent primarily on the surface area of the adsorbent since the dye molecule is small enough to penetrate nearly the entire pore system. To 25 ml. of a dye solution containing 1.0 gram of methylene blue per liter was added in separate runs 0.40 gram of the carbon particulate under test. After swirling the beaker containing the test sample for 30 seconds, the solution was allowed to stand for a total of 60 minutes before a solution aliquot was withdrawn for colorimetric analysis. Results are given in Table V.

TABLE V

| Carbon From Example | Surface Area $N_2BET$[1] | Dye Removed 1 hour (%) | Dye Removed % ÷ Surface Area |
|---|---|---|---|
| 4 | 550 | 34 | 0.062 |
| Comparative B | 580 | 32 | 0.055 |
| Comparative C | 1235 | 54 | 0.044 |

Note
[1] Meters² per gram

The results of Table V show that while the carbon of Comparative Example C removed the most dye, the carbon particulate of Example 4 of the present invention was the most effective based on available surface area.

B. Molasses

The decolorizing of a molasses solution is a measure of an adsorbent's ability to remove large color bodies and is often used as a characterization test.

A stock solution was prepared by dissolving 20 grams of blackstrap molasses in water to make 500 ml. of solution. To 100 ml. of the stock solution was added 0.50 gram of the carbon under test. The resulting composition was allowed to stand overnight in quiescent state. After 16 hours adsorption time, an aliquot of the test solution was centrifuged to remove carbon particles and the remaining color in the test solution was determined colorimetrically. Results are given in Table VI.

TABLE IV

| | PROPERTIES OF COMPACTED VERSUS AGGLOMERATED CARBONS | | | | | |
|---|---|---|---|---|---|---|
| EXAMPLE NO. | METHOD OF PREPARATION | SURFACE AREA M²/g. | PORE VOLUME cc/g. | CRUSH STRENGTH (lbs.) | MEDIAN PORE RADIUS A | % OF SURFACE AREA IN PORES ≦ 20 A |
| 8 | Extrusion | 496 | 0.70 | 2.1 | 56 | 55 |
| 9 | Pelleted | 531 | 0.80 | 1.1 | 40 | 50 |
| 10 | Roller Mill | 554 | 0.81 | — | 44 | 50 |
| Comparative D | Agglomerated | 20 | ≦0.1 | 2.3 | — | — |
| Comparative E | Agglomerated | 45 | ≦0.1 | 0.8 | — | — |

The data of Table IV show that compacting can be accomplished by various methods to provide the carbon particulates of the present invention. The data also show that the prior art procedure, Comparative Examples D and E, did not produce carbon particulates of desirable surface area and pore volume.

EXAMPLE 11

In this example, various carbon particulates were evaluated as selective adsorbents of various substances from solutions. All carbon particulates were of size 40 × 60 mesh. Representative of the carbon particulates of

TABLE VI

| Carbon From Example | Color Removed 16 Hours (%) |
|---|---|
| 4 | 37.5 |
| B | 37.5 |
| C | 7.5 |

The results of Table VI show that carbon particulates of Example 4 and comparative Example B are superior to the high surface area carbon particulate of Comparative Example C.

C. Permanganate

The adsorption of permanganate has been used as a measure of the decolorizing capacity of a carbon, although it is not clear whether the reduction in color in such case is due primarily to adsorption of the permanganate ion or reduction thereof to $MnO_2$ catalyzed by the carbon surface. 0.5 gram of the carbon particulate under test and the beaker containing same was then swirled for 30 seconds. The mixture was then allowed to stand for 2 hours after which an aliquot of the solution was removed for analysis. Results are given in Table VII.

TABLE VII

| Carbon from Example | $MnO_4$-Removed After 2 hours, (%) |
|---|---|
| 4 | 34 |
| Comparative B | 26 |
| Comparative C | 14 |

The results of Table VII show that the carbon particulate of the present invention is more effective for the removal of permanganate ion than either of the prior art absorbents.

We claim:

1. A process for adsorbing adsorbable materials from solution which comprises contacting said solution with a porous carbon particulate comprising carbon black spheres bonded in molded relationship by a carbonized binder, said spheres having an average diameter in the range of about 80 to 5000 angstrom units and a surface area of at least 100 square meters per gram, and said particulate having a pore volume of at least 0.2 cubic centimeters per gram, a surface area of at least 100 square meters per gram, said particulate surface area being equal to or less than the surface area of said spheres, and a pore size distribution such that at least about 45% of its total surface area is in pores of radius equal to or greater than 20 angstrom units.

2. A process of claim 1 wherein said solution flows through a fixed bed of said carbon particulate.

3. The process of claim 1 comprising the additional step of filtering off said carbon particulate.

* * * * *